United States Patent [19]

Grethe et al.

[11] 4,174,344

[45] Nov. 13, 1979

[54] PROCESS FOR THE PREPARATION OF METHYL 3,4-ANHYDRO-2,6-DIDEOXY-L-RIBO-HEXOPYRANOSIDE

[75] Inventors: Guenter Grethe, North Caldwell; Milan R. Uskokovic, Upper Montclair; John Sereno, Pine Brook, all of N.J.

[73] Assignee: Hoffmann-La Roche Inc., Nutley, N.J.

[21] Appl. No.: 850,982

[22] Filed: Nov. 14, 1977

[51] Int. Cl.$^2$ ............................................. C07D 301/00
[52] U.S. Cl. .................................. 260/348.55; 536/1; 260/343; 424/180; 536/4
[58] Field of Search ............... 260/348.55, 348.25; 424/120

[56] References Cited

U.S. PATENT DOCUMENTS

| | | | |
|---|---|---|---|
| 2,916,462 | 12/1959 | Koroch | 260/348.25 |
| 3,997,663 | 12/1976 | Pennert et al. | 424/120 |

OTHER PUBLICATIONS

Chem. Abstracts, 85, 62725d (1976).
Wong, C. M., et al., Con. J. Chem., 53,3144 (1975).
Cella, J. A., et al., J. Org. Chem., 42, 2077 (1977).
Corey, E. J. et al., Tetrahedron Lett., 311 (1970).
Richardson, A. C., Chem. Comm., 627 (1965).
March, J. P., et al., Chem. Comm., 973 (1967).
Horton, D. and Weckerle, W., Carboh Research, 44,227 (1975).
Partridge, J. J., et al., J. Amer. Chem. Soc., 95,532 (1973).

Primary Examiner—Johnnie R. Brown
Assistant Examiner—Blonde L. Hazel
Attorney, Agent, or Firm—Jon S. Saxe; Bernard S. Leon; Frank P. Hoffman

[57] ABSTRACT

A process to produce methyl 3,4-anhydro-2,6-dideoxy-L-ribohexopyranoside, its enantiomer and racemate thereof.

The compound is useful as an intermediate in the production of daunosamine which in turn is a prime constituent in the anti-cancer agents Daunomycin and Adriamycin. Also disclosed are novel intermediates in the process.

2 Claims, No Drawings

PROCESS FOR THE PREPARATION OF METHYL 3,4-ANHYDRO-2,6-DIDEOXY-L-RIBO-HEXOPYRANOSIDE

DESCRIPTION OF THE INVENTION

The present invention relates to a novel method to produce methyl 3,4-anhydro-2,6-dideoxy-L-ribo-hexopyranoside, its enantiomer and racemate thereof, which is useful as an intermediate in the production of daunosamine, a prime constituent in the anti-cancer agents, Daunomycin and Adriamycin. Also disclosed and claimed are several novel intermediates in the process.

The present novel process follows the following reaction scheme

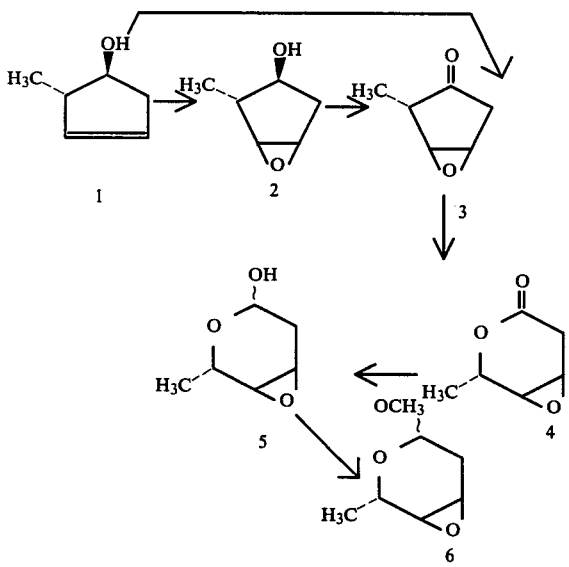

1→2

The compound of formula 1 is prepared following methods known in the art, for instance, from cyclopentadiene, see, for example, articles by Partridge et al., J. Amer. Chem. Soc., 95, 532 (1973). The reaction (1→2) is an oxidation utilizing aliphatic or aromatic peracids as the oxidizing agent. Useful aliphatic or aromatic peracids include peracetic acids, performic acid, trifluoroacetic acid, permaleic acid, perbenzoic acid, monoperphthalic acid, o-sulfoperbenzoic acid, p-nitroperbenzoic acid and m-chloroperbenzoic acid which is preferred. Also utilizable would be hydrogen peroxide in an acetic or alkaline medium or t-butylhydroperoxide in an alkaline medium.

Solvents suitable for the reaction are any inert inorganic solvent, such as, ether, chloroform, carbontetrachloride, dichloroethane, chloroethane, benzene, benzonitrile, acetonitrile, ethylacetate, acetone, pyridine or as preferred, methylene chloride. Also biphasic systems consisting of the above organic solvents and an aqueous alkaline medium may be used.

Useful as buffering agents in the oxidation reaction are sodium, potassium, calcium or magnesium formates, acetates or butyrates, sodium dihydrogenphosphate, disodium hydrogenphosphate or sodium, potassium, calcium or magnesium carbonate with sodium carbonate as preferred.

2→3

The above end product (2) is thereafter oxidized utilizing an oxidizing agent, such as, sodium or potassium dichromate in sulfuric acid, chromium trioxide in acetic or sulfuric acid or pyridine, or perbenzoic acids such as mentioned above in the presence of 2,2,6,6-tetramethylpiperidine. Preferred is chromium trioxide in aqueous sulfuric acid (Jones reagent).

Suitable solvents for the above reaction include inert organic solvents, such as, acetone, t-butanol, pyridine, acetonitrile, dimethylformamide, glacial acetic acid, petroleum ether, benzene, ether and carbon tetrachloride. Preferred is acetone.

3→4

The end product of the above reactive step (3) is thereafter oxidized utilizing an aliphatic or aromatic peracid as set forth in step 1→2. Also utilizable as an oxidizing agent is $H_2O_2$ in sulfuric acid or borontrifluoride. Preferred as the oxidizing agent is m-chloroperbenzoic acid.

Solvents which may be used in this reaction are inert organic solvents, such as, ethylacetate, methylene chloride or chloroform.

A buffering agent may be utilized in this reaction step. Useful buffering agents in this reaction step are the same as set forth in step 1→2. Preferred is sodium bicarbonate.

4→5

The end product of the above reactive step (4) is thereafter reduced to provide the 3,4-anhydro-2,6-dideoxy-L-ribo-hexose.

Useful reducing agents include DIBAL-H, diborane, sodium or lithium triethoxyaluminumhydride, sodium-bis [2-methoxyethoxy] aluminumhydride or tri-t-butoxyaluminohydride. Preferred as a reducing agent is DIBAL-H.

Solvents which may be used are aromatic hydrocarbons, such as, toluene, benzene and xylene or dioxane, bis-(2-methoxy)ethyl ether, tetrahydrofuran or other ethers. Preferred as a solvent is toluene.

1→3

An additional step which may be utilized to lessen the overall process steps involves the reaction of the comtpound of formula 1 with an aliphatic or aromatic peracid such as disclosed in step 1→2 followed by in situ addition of 2,2,6,6-tetramethylpiperidine to form in one step the product of formula 3. Inert solvents are as in step 1→2 and the preferred peracid is m-chloroperbenzoic acid.

5→6

The end product (3,4-anhydro-2,6-dideoxy-L-ribo-hexose) may thereafter be reacted to form an anomeric mixture of methyl 3,4-anhydro-2,6-dideoxy-L-ribo-hexopyranoside a prime well known intermediate in the synthesis of daunosamine. The compound is known in the literature, e.g., Marsh et al., Chem. Comm., 1967, 973. (see also Example 5)

The reaction is accomplished in methanol in the presence of an acidic catalyst, e.g., inorganic or organic acids, a cationic exchange resin or a Lewis acid ($BF_3$ preferred).

Thereafter the daunosamine may be produced following reactions known in the art, see, for example, Marsh et al., Chem. Comm., 1967, 973
Gupta, Carbohydrate Res., 37, 381 (1974)
Stevens et al., J. Org. Chem., 40, 3704 (1975)
Horton et al., Carbohydr. Res., 44, 227, (1975)

and daunomycin synthesized following the teaching of Acton et al., J. Med. Chem., 17, 659, (1974).

A teaching of the utility and use of the antibiotics Daunomycin and Adriamycin can be found in, for example, U.S. Pat. Nos. 3,997,663 and 3,590,028 respectively.

The following examples are illustrative of but should not be construed as limiting the present invention.

EXAMPLE 1

Preparation of (1S,2S,3S,5R)-2-Methyl-6-oxabicyclo[3.1.0]-hexan-3-ol

To a stirred mixture of 27.2 g (0.28 Mol) of (1S,2S)-2-methyl-3-cyclopenten-1-ol and 50 g of sodium bicarbonate in 400 ml of anhydrous methylene chloride was added at 0° over a period of 2 hr a solution of 58.3 g (0.29 mol) of 85% m-chloroperbenzoic acid in 1 L of anhydrous methylene chloride. After completed addition, stirring was continued for an additional 2 hr at 0° followed by the addition of 38 g of potassium carbonate and 60 ml of a saturated aqueous solution of potassium carbonate. The solids were collected by filtration and thoroughly washed with methylene chloride. Concentration of the filtrate under reduced pressure gave a liquid which after distillation afforded (1S,2S,3S,5R)-2-methyl-6-oxabicyclo[3.1.0]hexane-3-ol: bp 72°–75° (22 mm); $[\alpha]^{25}$ D +43.35° (c 1.169, $CH_3OH$).

EXAMPLE 2

Preparation of (1S,2S,5R)-2-Methyl-6-oxabicyclo[3.1.0]hexan-3-one

To a solution of 21.7 g (0.19 mol) of (1S,2S,3S,5R)-2-methyl-6-oxabicyclo[3.1.0]-hexan-3-ol in 450 ml of dry acetone was added at 0° during 8 min 90 ml of 1 N Jones reagent. The heavy suspension was stirred for an additional 8 min and subsequently poured onto 1 L of ice water. The mixture was extracted with 5×250 ml of methylene chloride. The combined extract was washed successively with a saturated aqueous solution of sodium bicarbonate and brine, dried over magnesium sulfate and evaporated to dryness to afford crude liquid (1S,2S,5R)-2-methyl-6-oxabicyclo[3.1.0]hexan-3-one. The combined crude material from several runs was distilled through a Vigreaux column to yield pure (1S,2S,5R)-2-methyl-6-oxabicyclo[3.1.0]hexan-3-one: bp 60°–66° (8 mm); $[\alpha]^{25}$ D +77° (c 1.10, MeOH).

EXAMPLE 3

Preparation of (1S,2S,6R)-2-Methyl-3,7-dioxabicyclo[4.1.0]-heptan-4-one

To a solution of 5.6 g (50 mmol) of (1S,2S,5R)-2-methyl-6-oxabicyclo[3.1.0]hexan-3-one (4) in 400 ml of anhydrous methylene chloride was added 15 g of sodium bicarbonate and 12.9 g (64 mmol) of 85% m-chloroperbenzoic acid. The suspension was stirred at room temperature for 72 hr and filtered through Celite Filter-Aid. The filtrate was evaporated to dryness under reduced pressure, the residue was triturated with 40 ml of methylene chloride and insolubles were removed by filtration. The filtrate was washed twice with a saturated aqueous solution of sodium bicarbonate, dried over magnesium sulfate and evaporated to dryness under educed pressure. Heating at 70° (0.1 mm) removed 0.95 g of volatile material. The oily residue slowly crystallized on standing to give (1S,2S,6R)-2-methyl-3,7-dioxabicyclo[4.1.0]heptan-4-one: mp 51°–52°. Recrystallization from 12 ml of ether yielded end product: mp 51°–52°. Several recrystallizations from ether gave analytically pure (1S,2S,6R)-2-methyl-3,7-dioxabicyclo-[4.1.0]heptan-4-one: mp 52.5°–53.5°; $[\alpha]^{25}$ D +147.26 (c 0.995, MeOH).

Anal. Calcd for $C_6H_8O_3$ (128.12): C, 56.25; H, 6.29. Found: C, 56.04; H, 6.43.

EXAMPLE 4

Preparation of 3,4-Anhydro-2,6-dideoxy-L-ribo-hexose {(1S,2S,6R)-2-methyl-3,7-dioxabicyclo[4.1.0]heptan-4-ol}

To a solution of 2.58 g (20 mmol) of (1S,2S,6R)-2-methyl-3,7-dioxabicyclo[4.1.0]-heptan-4-one in 300 ml of anhydrous toluene cooled to −75° was added under argon 14 ml (24.5 mmol) of a 1.75 M solution of DIBAL-H in toluene. The reaction mixture was stirred at −75° for 2 hr and then quickly poured onto a slurry of 260 g of silica gel (Silica Gel 60 Merck) in toluene and allowed to filter. The slurry was washed with 3 L of methylene chloride-methanol (9:1). The combined filtrate and washings were evaporated to dryness under reduced pressure. The residual oil was distilled with a Kugelrohr distillation apparatus to afford 3,4-anhydro-2,6-dideoxy-L-ribo-hexose: bp 90° (oven temperature) (0.1 mm); $[\alpha]^{25}$ D +25.16° (c 1.013, MeOH).

Anal. Calcd for $C_6H_{10}O_3$ (130.14): C, 55.37; H, 7.75. Found: C, 54.70; H, 7.67.

EXAMPLE 5

Preparation of Methyl 3,4-anhydro-2,6-dideoxy-L-ribo-hexopyranoside (anomeric mixture) {(1S,2S,6R)-4-methoxy-2-methyl-3,7-dioxabicyclo[4.1.0]heptane}

To a stirred solution of 8.8 g (68 mmol) of 3,4-anhydro-2,6-dideoxy-L-ribo-hexose in 150 ml of anhydrous methanol (distilled from 4Å molecular sieves) was added under a blanket of Argon at 35° 0.45 ml of a 8.8% (w/v) solution of boron trifluoride in methanol. The boron trifluoride solution was prepared just before use by passing boron trifluoride successively through concentrated sulfuric acid, sodium fluoride and boric acid anhydride and into anhydrous methanol. After addition of the boron trifluoride-methanol complex, the reaction mixture was stirred at 35° for 2 hr and then quenched by adding 2.5 g of sodium bicarbonate and stirring at room temperature for 0.25 hr. The solids were removed by filtration, the filter cake was washed with 3×10 ml of methylene chloride and the combined filtrate and washings were evaporated to dryness under reduced pressure to yield a semi-solid residue. This material was triturated with methylene chloride, solid material was removed by filtration and the filtrate was evaporated under reduced pressure. The residue was distilled through a Kugelrohr distillation apparatus at 90° (oven temperature) (0.1 mm) to yield the crude anomeric mixture of methyl 3,4-anhydro-2,6-dideoxy-L-ribo-hexopyranoside as a pale yellow liquid.

EXAMPLE 6

Preparation of (1S,2S,5R)-2-Methyl-6-oxabicyclo[3.1.0]hexan-3-one

To a stirred solution of 2.28 g (20 mmoles) of (1S,2S,3S,5R)-2-methyl-6-oxabicyclo[3.1.0]-hexan-3-ol and 1 ml (0.2 mmole) of a 0.2 M solution of 2,2,6,6-tetramethylpiperidine hydrochloride in a 1% mixture of ethanol in methylene chloride in 20 ml of methylene chloride was added, over 30 min, a solution of 6.20 g (30 mmoles) of 85% m-chloroperbenzoic acid in 100 ml of anhydrous methylene chloride. The reaction mixture was stirred at 0° for 1 hr. Half of the mixture was washed with 2×25 ml of 1 N sodium hydroxide and subsequently with brine. The organic layer was dried over magnesium sulfate, filtered, and evaporated to dryness under reduced pressure. The residue was distilled through a short-path distillation apparatus (bp 80°, 20 mm) to afford liquid (1S,2S,5R)-2-methyl-6-oxabicyclo[3.1.0]-hexan-3-one, identical (glpc, ir, nmr, tlc) with authentic material.

EXAMPLE 7

Preparation of (1S,2S,5R)-2-Methyl-6-oxabicyclo[3.1.0]hexan-3-one

To a stirred solution of 1.96 g (20 mmoles) of (1S,2S)-2-methyl-3-cyclopenten-1-ol in 20 ml of anhydrous methylene chloride was added, over 20 min, at 0° under an atmosphere of argon a solution of 4.44 (21.5 mmoles) of 85% m-chlorperbenzoic acid. After completed addition, the mixture was stirred for an additional 2 hr at 0°. The precipitate was removed by filtration and the filter cake was washed with methylene chloride. To the filtrate was added at 0° 4.5 g (22 mmoles) of solid 85% m-chlorperbenzoic acid and 1 ml (0.2 mmole) of a 0.2 M solution of 2,2,6,6-tetramethylpiperidine hydrochloride in a 1% mixture of ethanol in methylene chloride. The reaction mixture was stirred at 0° for 30 min. and subsequently for 2 hr at 35°. The precipitate was removed by filtration and the filtrate was washed with 2×20 ml of a saturated aqueous solution of sodium bicarbonate and subsequently with brine. The organic layer was dried over magnesium sulfate and evaporated to dryness under reduced pressure. Distillation of the residue in a Kugelrohr apparatus (80°, 20 mm) afforded (1S,2S,5R)-2-methyl-6-oxabicyclo[3.1.0]hexan-3-one, identical (tlc, ir, nmr) with authentic material.

What is claimed:

1. A compound of the formula

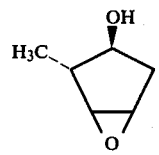

its enantiomer and racemate thereof.

2. A compound of the formula

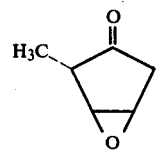

its enantiomer and racemate thereof.

* * * * *